United States Patent
Capuzzi et al.

(10) Patent No.: US 10,654,786 B2
(45) Date of Patent: May 19, 2020

(54) PROCESS FOR THE PREPARATION OF PURIFIED DICARBOXYLIC ACIDS

(71) Applicant: NOVAMONT S.P.A., Novara (IT)

(72) Inventors: Luigi Capuzzi, Novara (IT); Francesca Digioia, Barengo (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 16/306,178

(22) PCT Filed: Jun. 5, 2017

(86) PCT No.: PCT/EP2017/063617
§ 371 (c)(1),
(2) Date: Nov. 30, 2018

(87) PCT Pub. No.: WO2017/211766
PCT Pub. Date: Dec. 14, 2017

(65) Prior Publication Data
US 2019/0202768 A1    Jul. 4, 2019

(30) Foreign Application Priority Data
Jun. 6, 2016 (IT) .................... 102016000057753

(51) Int. Cl.
| | |
|---|---|
| *C07C 51/44* | (2006.01) |
| *C07C 67/31* | (2006.01) |
| *C07C 67/333* | (2006.01) |
| *C07C 51/09* | (2006.01) |
| *C07C 51/43* | (2006.01) |

(Continued)

(52) U.S. Cl.
CPC ............. *C07C 51/44* (2013.01); *C07C 51/09* (2013.01); *C07C 51/43* (2013.01); *C07C 67/05* (2013.01); *C07C 67/31* (2013.01); *C07C 67/333* (2013.01); *C07C 55/18* (2013.01); *C07C 69/48* (2013.01); *C07C 69/675* (2013.01); *C11C 1/04* (2013.01)

(58) Field of Classification Search
CPC ......... C07C 51/09; C07C 51/44; C07C 67/05; C07C 67/31; C07C 67/333; C07C 55/18; C07C 69/48; C11C 1/04
See application file for complete search history.

(56) References Cited

U.S. PATENT DOCUMENTS

| 5,380,928 A * | 1/1995 | Malek ..................... C07C 51/27 |
| | | 562/512.4 |
| 6,559,339 B1 * | 5/2003 | Costantini .............. C07C 51/42 |
| | | 562/593 |
| 8,222,438 B2 * | 7/2012 | Bastioli ................. C07C 51/245 |
| | | 554/132 |

FOREIGN PATENT DOCUMENTS

| CN | 101-279-909 A | 10/2009 |
| WO | WO-2008-138892 A1 | 11/2008 |

(Continued)

OTHER PUBLICATIONS

XP 002767106—Abstract for CN-101-279-909-A.

*Primary Examiner* — Yate' K Cutliff
(74) *Attorney, Agent, or Firm* — Polsinelli PC (57) ABSTRACT

This invention relates to a process for the purification of dicarboxylic acids obtained from the hydrolysis of carboxylic acid triglycerides having more than one acid functional group. The process comprises in particular the separation of at least some of the glycerine from the hydrolysis product in an aqueous phase, evaporating and/or distilling the resultant organic phase and recovering at least some of the evaporated and/or distilled dicarboxylic acids through at least one crystallisation operation.

20 Claims, 2 Drawing Sheets (51) Int. Cl.
*C07C 67/05* (2006.01)
*C11C 1/04* (2006.01)
*C07C 55/18* (2006.01)
*C07C 69/48* (2006.01)
*C07C 69/675* (2006.01)

(56) References Cited

FOREIGN PATENT DOCUMENTS

WO   WO 2011/080296 A1 *  7/2011  ........... C01C 51/245
WO   WO-2011/080296 A1    7/2011

* cited by examiner

PROCESS FOR THE PREPARATION OF PURIFIED DICARBOXYLIC ACIDS

CROSS REFERENCE TO RELATED APPLICATIONS

This application is the National Phase of Application No. PCT/EP2017/063617 filed Jun. 5, 2017, which claims priority to Application No. 102016000057753 filed in Italy on Jun. 6, 2016 under 35 U.S.C. § 119. The entire contents of each application are hereby incorporated by reference.

DESCRIPTION

TECHNICAL FIELD

This invention relates to a process for the preparation of purified dicarboxylic acids carried out by hydrolysing a mixture containing triglycerides with more than one acid functional group and subjecting the reaction product to a series of operations comprising at least one crystallisation.

BACKGROUND OF DISCLOSURE

Dicarboxylic acids may be prepared by processes of various kinds. High yields of carboxylic acids may for example be obtained from renewable sources with a low environmental impact through processes of the oxidative cleavage of unsaturated fatty acids and their derivatives originating from animal and plant oils and fats. Through these processes mixtures of monocarboxylic acids and dicarboxylic acids or their derivatives, which nevertheless require multiple and complex operations for their separation and purification, are obtained.

In particular, when triglycerides containing unsaturated fatty acids, such as for example those present in vegetable oils, are subjected to oxidative cleavage processes, mixtures of monocarboxylic acids and triglycerides containing saturated carboxylic acids with more than one acid functional group are obtained. Patent application WO 2008/138892 describes for example a process in which a fraction of monocarboxylic acids is separated from the oxidative cleavage product of vegetable oils through one or more evaporation and/or distillation operations, depending upon the level of purity required. In patent application WO 2011/080296 the remaining mixture containing triglycerides with more than one acid functional group subsequently undergoes hydrolysis to release further carboxylic acids from the triglycerides containing them. The product obtained nevertheless still contains a mixture of monocarboxylic and dicarboxylic acids and therefore requires further purification steps to obtain dicarboxylic acids which can be used in applications requiring a high degree of purity, such as for example use as monomers in polymerisation reactions.

SUMMARY OF DISCLOSURE

A process for the preparation of dicarboxylic acids which makes it possible to obtain high purity dicarboxylic acids has now been developed. The dicarboxylic acids obtained through this process are in fact characterised by a monocarboxylic acids content such that they can be used in polymerisation reactions without further purification treatments.

Thanks to the particular sequence of operations distinguishing it, the process according to the invention also makes it possible to achieve appreciable efficiency in separation operations and as a consequence high product recovery yields.

More particularly the object of this invention is a process for the preparation and isolation of dicarboxylic acids starting from a mixture containing carboxylic acid triglycerides having more than one acid functional group comprising the steps of:
a) hydrolysing the said mixture containing triglycerides in the presence of water, obtaining a reaction product comprising dicarboxylic acids and glycerine;
b) separating out an aqueous phase containing at least part of the glycerine from an organic phase containing the remaining reaction product from step a);
c) evaporating and/or distilling the organic phase obtained in step b), separating out a residue;
d) recovering at least some of the dicarboxylic acids from the organic phase evaporated and/or distilled in step c) by means of at least one crystallisation operation.

According to a preferred aspect of the invention said recovery step d) comprises the operations of:
d1) extracting the organic phase evaporated and/or distilled from step c) with water and at least one organic solvent, obtaining an aqueous phase containing the said dicarboxylic acids;
d2) crystallising the said dicarboxylic acids out from the said aqueous phase obtained in step d1).

According to another aspect of the invention said recovery step d) comprises at least one operation of crystallising the said dicarboxylic acids from a melt.

BRIEF DESCRIPTION OF THE SEVERAL VIEWS OF THE DRAWINGS

The process in question will be described in detail below.

DETAILED DESCRIPTION OF DISCLOSURE

Figure 1:
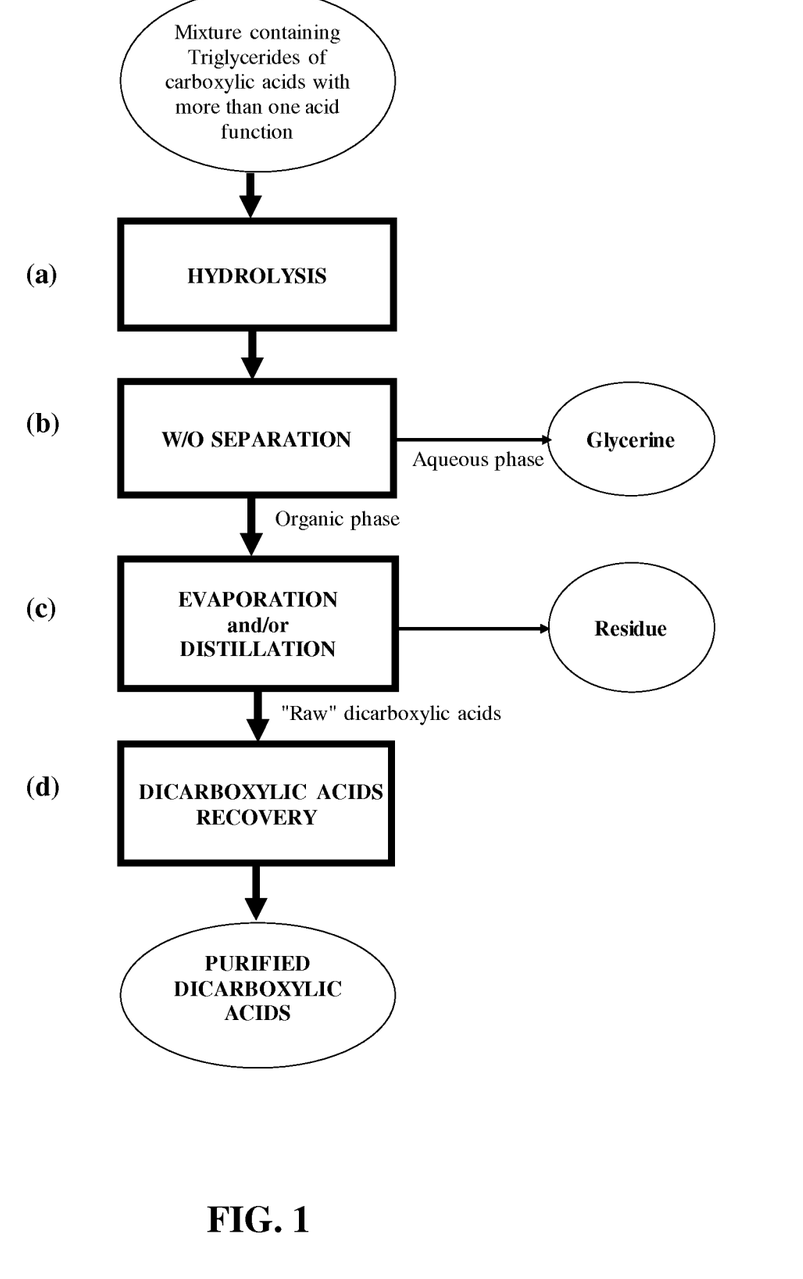
FIG. 1 shows a flow diagram of one possible configuration of the process.
Figure 2:
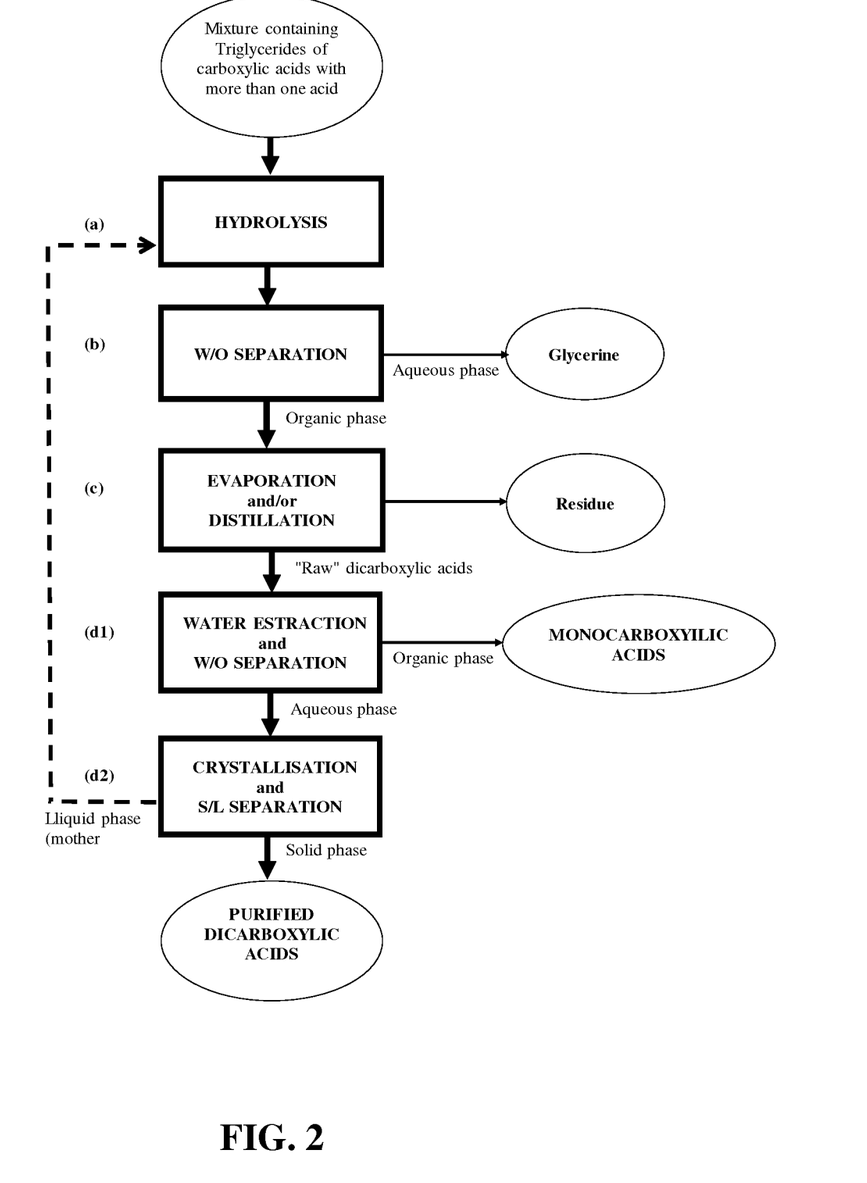
FIG. 2 shows a preferred configuration of the process in which the crystallisation mother liquors separated in step d2) are recycled to hydrolysis step a).

The mixture containing carboxylic acid triglycerides having more than one acid functional group suitable for use as a starting material in this process is a mixture comprising one or more triglycerides which are the same or different and contain at least one acyl group of a dicarboxylic acid.

Suitable dicarboxylic acids are aliphatic diacids, preferably saturated and preferably of the alpha-omega type, selected for example from oxalic acid, malonic acid, succinic acid, glutaric acid, adipic acid, pimelic acid, suberic acid, azelaic acid, sebacic acid, undecanedicarboxylic acid, dodecanedicarboxylic acid, brassylic acid, tetradecanedicarboxylic acid or pentadecanedicarboxylic acid. Advantageously the said dicarboxylic acids have a $C_6$-$C_{24}$ chain and preferably belong to the group comprising suberic acid, azelaic acid, sebacic acid, undecanedicarboxylic acid, dodecanedicarboxylic acid, brassylic acid and mixtures thereof.

According to a preferred aspect of the invention the mixture of triglycerides used as a starting material mainly contains azelaic acid.

In addition to the abovementioned acyl dicarboxylic acid groups the said triglycerides also typically contain one or more acyl monocarboxylic acid groups which are the same or different. The said monocarboxylic acids are aliphatic monoacids and may be saturated or unsaturated, substituted or unsubstituted; they have a chain typically of length $C_6$-$C_{24}$ and more commonly $C_9$-$C_{24}$. Saturated monocarboxylic acids are preferred. Examples of unsubstituted monocarboxylic acids are palmitic, stearic, oleic, arachic, behenic and lignoceric acids.

Examples of substituted monocarboxylic acids are long chain monocarboxylic acids having one or more ketone groups or hydroxyl groups in a non-terminal position such as $C_{12}$-$C_{24}$ carboxylic acids containing at least one ketone group or $C_{12}$-$C_{24}$ hydroxy acids containing at least one secondary hydroxyl group. Specific examples of substituted monocarboxylic acids which may be present are 9-hydroxystearic acid, 9-ketostearic acid, 10-ketostearic acid and 10-hydroxystearic acid.

The said substituted monocarboxylic acids may contain two adjacent hydroxyl groups, such as dihydroxypalmitic, dihydroxystearic, dihydroxyoleic, dihydroxyarachic and dihydroxybehenic acids, or a hydroxyl group adjacent to a ketone group.

The mixture containing carboxylic acid triglycerides having more than one acid functional group used as a starting material in this process also optionally contains one or more free monocarboxylic and/or dicarboxylic acids.

Examples of monocarboxylic acids which may be found free in the mixture are saturated or unsaturated aliphatic monoacids having a linear or branched chain of between $C_2$ and $C_{24}$, which may or may not be substituted.

Examples of dicarboxylic acids which may be found free in the mixture correspond to those listed above with possible triglyceride acyl substituents.

Triglycerides of carboxylic acids with more than one acid functional group present in the starting mixture may advantageously be obtained for example from unsaturated triglycerides present in vegetable oils or animal fats, using known techniques. One example is the oxidative cleavage reactions of the double bonds present in the acyl groups of the said unsaturated triglycerides. These reactions may be carried out using one or more oxidising agents such as for example inorganic and organic peroxides, peracids, nitric acid, permanganates, periodates, $O_2$, $O_3$ or mixtures of gases containing them.

Mixtures of triglycerides obtained by processes of the oxidative cleavage of unsaturated triglycerides in which peroxides such as hydrogen peroxide and $O_2$ or mixtures containing $O_2$ are used are in particular advantageously used as a starting material. Preferred examples are the processes described in applications WO 2008/138892, WO 2011/080296 or WO 2013/079849 A1.

Particularly preferred are the mixtures of triglycerides containing dicarboxylic acids obtained after step c) of separating out saturated monocarboxylic acids through the processes described in applications WO 2008/138892 and WO 2011/080296, which are incorporated herein as a reference.

This invention therefore also relates to a process for the production of purified carboxylic acids comprising, before step a) the steps of:
1) reacting the said triglycerides of unsaturated carboxylic acids with an oxidising agent and a catalyst activating the oxidisation reaction of the olefin double bond in order to obtain an intermediate compound containing vicinal diols, and
2) causing the said intermediate compound containing vicinal diols, an oxidising agent containing molecular oxygen and a catalyst activating the oxidation reaction of vicinal diols to carboxylic groups to react, obtaining monocarboxylic acids and triglycerides of carboxylic acids with more than one acid functional group;
3) separating, preferably by distillation, a fraction of the said monocarboxylic acids obtaining a mixture comprising the said triglycerides of carboxylic acids with more than one acid functional group.

Unsaturated carboxylic acid triglycerides suitable for use in abovementioned step 1) contain monounsaturated and/or polyunsaturated carboxylic acids, such as for example, 9-tetradecenoic (myristoleic) acid, 9-hexadecenoic (palmitoleic) acid, 9-octadecenoic (oleic) acid, 12-hydroxy-9-octadecenoic (ricinoleic) acid, 9-eicosenoic (gadoleic) acid, 13-docosenoic (erucic) acid, 15-tetracosenoic (nervonic) acid, 9,12-octadecadienoic (linoleic) acid, and 9,12,15-octadecatrienoic (linolenic) acid. Preferred are triglycerides containing monounsaturated carboxylic acids; the use of oleic acid triglycerides from the oxidative cleavage of which mainly triglycerides of azelaic acid are obtained is particularly advantageous according to this aspect of the process.

The said triglycerides of unsaturated carboxylic acids are preferably present in vegetable oils or mixtures thereof, which therefore constitute the preferred raw material fed to the process according to this aspect of the invention. By vegetable oils are meant both the unmodified product of pressing or the oil which has undergone chemical or chemical-physical modifications, such as for example, purification, hydrogenation or enzyme enrichment treatments. Examples of preferred vegetable oils are soya oil, olive oil, castor oil, sunflower oil, peanut oil, maize oil, palm oil, jatropha oil, *Cuphea* oil, oils from Brassicaceae, such as *Crambe abyssinica, Brassica carinata, Brassica napus* (colza), Carduae oils such as *Cynara cardunculus* (thistle), *Silybum marianum, Carthamus tinctorius, Lesquerella*, and other oils having a high monounsaturated acids content. The use of sunflower oil and thistle oils is particularly preferred.

The oxidising agent used to carry out step 1) (hydroxylation) is selected from osmium tetroxide, permanganates, hydrogen peroxide, alkyl-hydroperoxides and percarboxylic acids, such as for example performic acid, peracetic acid or perbenzoic acid. The said oxidising agent is more preferably an aqueous solution of hydrogen peroxide in concentrations of between 30 and 80% by weight, preferably between 40 and 70% and even more preferably between 49 and 65%.

The diol resulting from hydroxylation step 1) is caused to react—during oxidative cleavage step 2)—with oxygen or a compound containing oxygen. The use of air is particularly advantageous. Air enriched with oxygen may also be used.

The catalyst for step 1 belongs to the group of transition elements. Fe, Mn, Mo, Nb, Os, Re, Ti, V, W, Zr and their acids, alkali metal salts and complexes are advantageously used as homogeneous or heterogeneous phase catalysts, possibly in supported or nanostructured form. The use of tungstic acid and/or its derivatives, such as phosphotungstic acid, is particularly preferred. The said catalyst is present in quantities of between 0.03% and 3% in moles, preferably between 0.05% and 1.8% in moles, and even more preferably between 0.06% and 1.5% in moles with respect to the total moles of unsaturations.

As far as the catalyst for step 2) of oxidative cleavage is concerned, this belongs to the group of transition elements. Ce, Cr, Co, Cu, Mn, Mo, Re, Os, V and W and their acids, alkali metal salts and complexes are advantageously used as homogeneous phase catalysts. The use of cobalt suits such as, for example, acetate, chloride, sulfate, bromide and nitrate, used in quantities between 0.05% and 3% in moles, preferably between 0.1% and 2% in moles and even more preferably between 0.3% and 1.5% in moles with respect to the diol produced in step 1) is particularly preferred. Particularly preferred is the use of cobalt acetate and cobalt chloride.

An inorganic acid, for example, phosphoric acid, sulfuric acid, hydrochloric acid, perchloric acid and mixtures thereof may be added to the catalyst in step 2).

At the start of step 1) a small quantity of the intermediate compound obtained at the end of step 1) itself may be added, as the diols present in it encourage activation of the reaction. The said intermediate compound may be added in a quantity of ≤5%, preferably ≤3% by weight with respect to the starting oil.

Advantageously, during the course of step 1) of the process according to the invention air or inert gas (e.g. nitrogen) are caused to flow in order to remove part of the water produced in the process and to avoid excessive dilution of $H_2O_2$. An alternative to the flow of these gases is evaporation under vacuum.

The reaction temperatures for step 1) and step 2) advantageously lie between 45 and 95° C., preferably between 50 and 90° C. In particular, the reaction temperature in step 1) is advantageously between 55 and 80° C., while the reaction temperature in step 2) is advantageously between 55 and 90° C., even more advantageously between 60 and 80° C.

Advantageously, when carrying out both step 1) and step 2) of this process, the reaction time (that is the average residence time in the reactors in the case of a continuous process) is between 2 and 8 hours for each step.

In a preferred embodiment of the process the intermediate product resulting from step 1), containing vicinal diols, is fed directly to the reactor in which step 2) is carried out. The effect is an advantageous decrease in reaction time, thanks to the greater reactivity of the intermediate product itself, together with a significant increase in reaction yield.

Steps 1-2) of the process may advantageously be carried out at atmospheric pressure or, in any event, moderate oxygen partial pressures, with obvious advantages from the point of view of industrial production.

Step 1) is preferably carried out at atmospheric pressure or under slight vacuum.

Step 2) is preferably carried out with air at a pressure of ≤50 bar, preferably ≤30 bar.

According to one aspect of the invention these steps 1-2) are carried out in continuous reactors. The use of such continuous reactors makes it possible to reduce reaction volumes, aiding the exchange of heat. In a preferred embodiment one or more reactors of the CSTR (Continuous Stirred-Tank Reactor), possibly placed in series, are used.

Continuous reactors of the gas/liquid type are advantageously used in step 2). External recirculation (Loop CSTR) reactors, which encourage contact between the oxidising agent in the gaseous phase and the reaction mixture in the liquid phase, are preferably used when air is the oxidising agent.

Both steps 1) and 2) are preferably carried out without the addition of organic solvents.

The intermediate product obtained from step 1) is fed to step 2), where it is caused to react with oxygen or a compound containing oxygen without the need for any purification treatment.

In a preferred embodiment of the process the catalyst is not removed at the end of step 1).

In a preferred embodiment of the process step 2) is carried out without the addition of water, apart from that in which the catalyst is dissolved. Advantageously said step 2) comprises an aqueous phase and an organic phase having a water/diol ratio by weight which is advantageously kept below 3:1, preferably below 1:1 and more preferably below 1:3 throughout the time of the oxidation reaction.

Advantageously, the aqueous phase is separated from the organic phase at the end of step 2). The aqueous phase can contain the catalysts for steps 1) and 2), and these in turn may be recovered and optionally recycled, possibly after suitable preliminary treatments, as catalysts for step 1) or step 2). One example of a preliminary treatment which makes it possible to reuse tungsten-based catalysts in step 1) is described in patent application WO 2016/116479.

In an alternative embodiment of the process the aqueous phase separated at the end of oxidative cleavage step 2) containing the catalysts for steps 1) and 2) is fed back to the reactor for step 2), together with or as an alternative to fresh catalyst, after the addition of a suitable quantity of base, as described in International patent application PCT/EP2017/063613, incorporated here as a reference.

In a preferred embodiment of the process in which oil having a high oleic content is used as the starting material, the organic phase substantially comprises pelargonic acid and triglycerides of azelaic, palmitic, stearic and dihydroxystearic acids.

In another embodiment of the process in which the starting material is oil having an high monounsaturated acid content obtained by partial hydrogenation, the organic phase typically comprises medium-short monounsaturated acids and triglycerides of azelaic, sebacic, undecandioic, dodecandioic, palmitic, stearic and dihydroxystearic acids.

In step 3) of the process, the organic phase obtained as the oxidative cleavage product is fed to equipment suitable for separating the saturated monocarboxylic acids from the triglycerides containing saturated carboxylic acids having more than one carboxyl functional group. The separation is advantageously performed by means of distillation and/or evaporation processes. All distillation and/or evaporation processes which do not result in strong thermal stress on the mixture of products obtained in step 2), such as for example distillation in the flow of steam, molecular distillation, or evaporation in thin film or falling film evaporators are preferred. In a preferred embodiment of the process the monocarboxylic acids are separated from the triglycerides by evaporation using thin film evaporators.

The mixture obtained in step 3) listed above is then fed to the hydrolysis reaction in step a) of the process according to this invention.

During step a) of the process according to this invention the starting material containing carboxylic triglycerides having more than one acid functional group undergoes a hydrolysis reaction. This reaction may be performed through the use of different techniques, for example by feeding water alone or steam to the hydrolysis reactor, in the presence or absence of catalysts of the acid or enzyme type or by means of strongly acid ion exchange resins.

In the case of hydrolysis using water (or steam), the reaction advantageously takes place at temperatures between 150 and 350° C., preferably between 180 and 320° C., and at pressures typically between 10 and 200 bar, with or without the addition of a catalyst. The water/organic phase ratio by weight preferably lies between 1:2 and 5:1, more preferably between 1:1 and 5:1.

Hydrolysis using strongly acid ion exchange resin is performed at a temperature of 100-120° C. Examples of suitable resins are those of the Amberlyst® and Amberlite® type (both manufactured by Rohm and Haas Co.).

In the case of the reaction catalysed by enzymes (lipases), lipases selected from the group comprising: *Candida cylindracea, Candida antartica, Pseudomonas* sp., porcine pancreatic lipases, *Candida rugosa, Geotrichum candidum, Aspergillus niger, Mucor mietei, Rhizopus arrhizus, Rhizopus delemar, Rhizopus niveus, Chromobacterium viscosum, Thermomyces lanuginosus,* or *Penicillum cyclopium* may advantageously be used.

In a preferred form of the process the hydrolysis reaction is carried out using only water at 240-320° C. and at pressures between 40 and 110 bar.

According to a particularly preferred aspect of the invention this reaction is carried out at a temperature of preferably between 260 and 310° C. and pressures preferably between 67 and 100 bar in one or more tubular reactors (Plug Flow Reactors).

The ratio between the quantity of water (aqueous phase) and the starting material (organic phase) is advantageously between 1:1 and 5:1 by weight, preferably greater than or equal to 2:1. The aqueous phase and organic phase are advantageously premixed and preheated, preferably up to a temperature of at least 240° C. before being fed to the hydrolysis reactor. The said preheating may for example advantageously be brought about by recovering heat from the product leaving hydrolysis step a).

The aqueous phase and the organic phase are passed to the hydrolysis reactor and heated to a temperature of 260-310° C., preferably of between 270 and 305° C., in times of preferably less than 10 minutes, more preferably between 2 and 5 minutes.

The hydrolysis reaction is then advantageously performed by holding the reagents at temperatures 260-310° C., preferably of between 270 and 305° C. for times of less than 30 minutes, preferably between 15 and 25 minutes.

One advantage of this aspect of the process lies in the fact that the reaction can be effectively performed in the absence of catalysts or other additives such as for example surfactants, which would require subsequent separation from the reaction product, without subjecting the starting mixture to preliminary treatments.

The reaction may however be further eased for example by adding surfactants and/or catalysts such as organic or inorganic acid catalysts. Examples of suitable inorganic acids are sulfuric, hydrochloric, perchloric, nitric, phosphoric, or hydrofluoric acids; examples of organic acids are methane sulfonic, naphthalene sulfonic or toluene sulfonic acids, preferably low molecular weight carboxylic acids such as formic, acetic or propionic acids, heterogeneous acids such as strongly acid ion exchange resins and supported transition metals, for example catalysts supported on a zirconium base.

In a preferred embodiment of the process hydrolysis step a) performed by mixing a suitable quantity partial esters of glycerine to the starting triglycerides, with further advantages in terms of yield and the economic nature of the process, as described in International patent application PCT/EP2017/063615, incorporated herein as a reference.

The product leaving the hydrolysis reactor typically contains glycerine, dicarboxylic acids, monocarboxylic acids and a quantity of water which may vary according to the hydrolysis conditions used.

During step b) the aqueous phase containing glycerine together with a variable quantity of carboxylic acids present in the hydrolysis product, which may be water soluble, are separated out from the remaining part of the hydrolysis product in the organic phase. This operation is performed in accordance with procedures known to those skilled in the art, for example by decanting or centrifuging. In the case where the triglycerides which have undergone hydrolysis mainly include azelaic acid the separation is typically performed by decanting, preferably by bringing the hydrolysis product to a temperature of between 60 and 90° C. and a pressure close to atmospheric (approximately 1 bar).

The separation in step b) preferably comprises one or more operations selected from degassing, washing with water, in addition to that fed during the reaction in step a), and/or the addition of suitable quantities of organic solvents which are immiscible with water. These operations have the effect of assisting separation of the aqueous phase from the organic phase. Examples of suitable solvents for assisting separation of the aqueous phase from the organic phase are hydrocarbons such as hexane, octane, nonane or mixtures thereof.

The addition of octane in a quantity of less than 10%, preferably less than 5% and over 2% with respect to the weight of the hydrolysis product is particularly advantageous.

According to one aspect of the process the aqueous phase is separated out following degassing and decanting.

The operation of decanting the two phases may be performed one or more times, possibly adding fresh water and carrying out one or more successive washes of the separated organic phase, for example counter-currently.

The aqueous phase separated out in step b) may then undergo purification and concentration treatments for the recovery of glycerine, any carboxylic acids which may be dissolved in it and any impurities present.

According to a preferred embodiment, the aqueous phase separated in step b) is purified by means of one or more crystallization operations to recover the dicarboxylic acids contained therein. For this purpose, the aqueous phase is typically brought to supersaturation by one or more operations selected, for example, from evaporation, direct or indirect cooling, chemical reaction, salting out. The skilled in the art is able to select the more appropriate method depending on the solubility of the system. Preferably, the said aqueous phase undergoes evaporative crystallization or cooling.

A particularly advantageous procedure consists in the evaporative crystallization of the said aqueous phase by heating it under reduced pressure. For example, water is evaporated at below 100 mbar, preferably below 150 mbar and more preferably between 160 and 250 mbar (corresponding to a boiling temperature of around 60-65° C.). The skilled person will easily determine the amount of water to be evaporated to achieve the conditions of supersaturation on the basis of the solubility of the dicarboxylic acid in the mixture and of the desired purity.

The crystallized dicarboxylic acids are then separated by the mother liquor, e.g. by centrifugation or filtration, and optionally washed to obtain the desired purity. According to a particularly advantageous aspect of the invention, the crystallized dicarboxylic acids are further purified by at least one of the crystallization operations of step d).

The organic phase separated out in step b) essentially comprises saturated carboxylic acids with one or more acid functional groups (i.e. monocarboxylic and dicarboxylic acids), which may or may not be substituted (e.g. with hydroxyl and ketone groups) and which might have been released during the hydrolysis reaction, and triglycerides and their oligomers deriving from incomplete hydrolysis of the initial mixture. It may also contain residues of water and organic solvent which are advantageously removed before passing on to the subsequent steps in the process, according to known techniques, for example by evaporation.

In step c) of the process the said organic phase undergoes one or more evaporation and/or distillation operations in order to separate out at least one fraction rich in dicarboxylic acids from a high boiling point residue.

According to one aspect of the process, at least one evaporation or distillation operation is performed under conditions not involving strong thermal stress on the organic phase, such as for example evaporation in thin film or falling film evaporators, distillation in a current of steam or molecular distillation. Advantageously the said operation is performed in thin film evaporators at temperatures which vary according to the composition of the mixture fed. For example when the process is performed starting with a mixture of acid triglycerides such as that obtained by the oxidative cleavage of oils having a high oleic acid content, the operation is advantageously carried out in thin film evaporators discharging the bottom product at a temperature not above 250° C. at a pressure of 5 mbar.

The high boiling point residue obtained in step c), comprising triglycerides and oligomers, can be collected and recycled to the hydrolysis reaction or can again undergo oxidative cleavage. It also finds application for the production of biofuels, biolubricants, plasticisers, extender oils for elastomers, monomers or components for plastics materials, bitumens and inks.

According to a preferred aspect of the process, in addition to the above mentioned high boiling point residue, a fraction containing monocarboxylic acids is also separated out from the said organic phase during step c).

The said organic phase can in fact undergo a further evaporation and/or distillation operation to separate out a first fraction comprising monocarboxylic acids from a second fraction rich in dicarboxylic acids. Advantageously this operation is performed in a fractionating column. In the abovementioned case in which the process is performed starting with a mixture of acid triglycerides obtained from highly oleic oil, the operation is preferably performed by discharging the bottom product at a temperature of not more than 210° C. at a pressure of 3 mbar. Through this procedure, a first fraction of distillate containing mainly monocarboxylic acids of chain length $C_9$ or shorter can for example be separated out at temperatures of 70-115° C. at 3 mbar. The second fraction rich in dicarboxylic acids so obtained comprises monocarboxylic acids having a chain length longer than $C_9$, which may be substituted (fatty acids and ketoacids).

The said fraction rich in dicarboxylic acids can be further purified by distillation, taking advantage of the different boiling points of any impurities in comparison with the dicarboxylic acids of interest, obtaining a purified fraction having a monocarboxylic acids content which may even be below 15% by weight.

These distillation operations make it possible to separate out a flow rich in more highly boiling point compounds from the base of the column, which can be recycled by pooling it with the flow from step b) and again subjecting it to evaporation and/or distillation in step c) of the process to recover the acids contained therein.

The fraction rich in dicarboxylic acids evaporated and/or distilled in step c) of this process then undergoes step d) through which the purified dicarboxylic acids can be recovered. According to a preferred embodiment of the invention this recovery comprises at least one operation of the extraction in water of the dicarboxylic acids which are soluble in an aqueous phase, performed in the presence of an organic solvent (step d1) and subsequent crystallisation of the dicarboxylic acids from the aqueous phase so obtained (step d2).

According to a preferred aspect of the invention, during step d1) at least one extraction operation is performed, sending a fraction rich in dicarboxylic acids to an extraction column under counter-current conditions with respect to the solvent water. This method of operation makes it possible to achieve effective extraction even when small quantities of water are used and in the absence of any organic solvent.

The extraction operations in step d1) take place at temperatures which vary according to the melting point of the fraction rich in dicarboxylic acids and the solubility of the dicarboxylic acid which it is intended to purify; these are typically between 50 and 90° C. In the case where azelaic acid is purified, extraction temperatures are preferably between 65 and 90° C. at atmospheric pressure.

According to one aspect of the invention step d1) comprises a single extraction operation performed in the presence of water and an organic solvent.

Organic solvents which are suitable for use in step d1) are aliphatic and/or aromatic hydrocarbons and/or mixtures thereof and may be selected from the group comprising linear or branched, cyclic or acyclic aliphatic alkanes and alkenes such as for example hexane, cyclohexane, hexene, cyclohexene, methylcyclopentane, methylcyclopentene, 2,2,4-trimethylpentane, methylcyclohexane, heptane, heptene, octane, nonane, isooctane; aromatic hydrocarbons such as for example benzene, toluene, xylene and the like, optionally substituted with alkyls having from 1 to 6 carbon atoms, or mixtures such as for example petroleum ether and naphtha.

Organic solvents which are particularly suitable for assisting the extraction of monocarboxylic acids from the aqueous phase are octane, nonane and mixtures thereof.

According to another aspect of the invention step d1) comprises two or more extraction operations. Preferably this comprises one preliminary extraction operation in the absence of organic solvent and a second extraction operation in the presence of organic solvent. More preferably according to this aspect step d1) comprises:
  (i) a preliminary extraction operation, performed by placing the unrefined dicarboxylic acid fraction originating from step c) in contact with a quantity of water such as to obtain a ratio by weight between the aqueous phase and the organic phase which lies between 1:1 and 10:1 at a temperature of preferably between 75 and 90° C. at atmospheric pressure and separating out a first organic phase comprising the monocarboxylic acids from a first aqueous phase comprising dicarboxylic acids;
  (ii) a second extraction operation, performed by placing the said first aqueous phase comprising dicarboxylic acids in contact with an organic solvent and separating out a second organic phase comprising monocarboxylic acids from a second aqueous phase comprising dicarboxylic acids.

According to a particularly advantageous aspect of the invention the said preliminary extraction operation (i) is carried out in a counter-current extraction column using a water:organic phase ratio of 6:1 and 4:1 by weight, preferably between 5.5:1 and 4.5:1. This water/organic phase ratio by weight represents the minimum quantity of aqueous phase which is able to maintain high selectivity for dicarboxylic acids, which are nevertheless wholly carried into solution, with a consequent high yield of product.

One type of extractor which is particularly suitable for carrying out the said first extraction operation (i) is a column with rotating stirrers, with pulsing plates or perforated plates which can be subdivided into two or more extraction sections.

Advantageously the second extraction operation (ii) described above can also be carried out in an extraction column, passing the said organic solvent counter-currently with respect to the aqueous phase. The ratio by weight between aqueous phase and the organic solvent is preferably between 15:1 and 5:1.

According to a particularly preferred configuration of the process in which octane is used as organic solvent a product having a monocarboxylic acids content of less than 0.5% by weight can be isolated from the aqueous phase.

Those skilled in the art will be easily able to adjust the temperature of the type (ii) extraction operations on the basis of the boiling point of the organic solvent used, the type of dicarboxylic acid which it is intended to purify and the possible formation of azeotropes. For the purification of azelaic acid for example, if octane is used the type (ii) extraction is advantageously performed at temperatures between 70 and 85° C.

According to one aspect of the invention the aqueous phase obtained following the extraction operations in step d1) is separated from the organic phase according to techniques known in the art, for example as described previously in respect of step b).

In step d2) the dicarboxylic acids extracted in the aqueous phase are crystallised from solution.

Crystallisation may be performed in either batch or continuous systems, in crystallisers of any configuration known in the art (e.g. cooled, evaporation, simple agitation, forced circulation, turbulent and fluidised bed crystallisers).

According to a preferred aspect of the invention the said crystallisation is preferably performed in a fractionated manner, that is subjecting the mixture requiring treatment to successive evaporation stages using at least two crystallisers placed in series and operating under different temperature and pressure conditions to allow optimum distribution and purification of the dicarboxylic acid.

Those skilled in the art may readily identify the operating conditions on the basis of the composition of dicarboxylic acid which has to be purified. For example, the crystallisation of azelaic acid from aqueous solution is advantageously performed using two crystallisers placed in series operating the first at an absolute pressure of between 200 and 100 mbar, preferably between 180 and 120 mbar, and the second at an absolute pressure which is even lower and dependent on the quantity of azelaic acid residue in the mother liquors of the first crystallisation, for example below 50 mbar.

According to one aspect of the process the fractionated crystallisation is combined with a solid/liquid separation system using techniques known to those skilled in the art, for example centrifuging and/or decanting.

The crystallisation mother liquors thus separated from the crystals advantageously have a quantity of dicarboxylic acids in solution which is below 1% by weight, even more advantageously below 0.8% by weight.

According to one particularly advantageous aspect of the invention the crystallisation mother liquors separated in step d2) of the process are recycled to hydrolysis step a). Reuse of the crystallisation mother liquors in the hydrolysis step in fact makes it possible to reduce the quantity of fresh water required in order to carry out the process. Also this operation makes it possible to recover a further fraction of carboxylic acids remaining in solution in the mother liquors, without further processing being required, thus guaranteeing a high yield of product.

According to one embodiment of the invention at least some of the crystallisation mother liquors are recycled to extraction step d1).

According to an alternative embodiment of the invention the recovery of dicarboxylic acids from step d) comprises at least one operation of crystallisation from a melt (melt crystallisation), either in suspension or on a cold surface. Such a form of realization is particularly advantageous as it allows operating effectively in the absence of solvents. This embodiment has the particular advantage that the dicarboxylic acids can be obtained directly in very high purity without the need for further washings and solvent extractions.

The said melt crystallisation is preferably carried out in a fractionated manner, i.e. subjecting the mixture requiring treatment to successive partial solidifications and remeltings so as to heighten the distribution between the liquid phase and the solid phase and thus remove impurities from the liquid phase.

According to one aspect of this embodiment of the process the fractionated crystallisation is combined with a solid/liquid separation system in a wash column.

The said column is particularly efficient in the case of the purification of azelaic acid obtained from oils with a high oleic content, as a result of which high yields can be obtained even in single stage processes (operating between 95 and 110° C. for example) and even higher when operating in two stages, as a result of behaviour during crystallisation and good filtration properties.

For example, by subjecting a fraction containing approximately 60% of azelaic acid by weight to a first melt crystallisation stage in suspension at temperatures of between 85 and 95° C. a fraction which is enriched to approximately 90% by weight can be obtained. This fraction can be further enriched, even exceeding 98% by weight of azelaic acid, following a second melt crystallisation stage in suspension at temperatures between 100 and 115° C.

According to another embodiment of the invention the recovery of dicarboxylic acids from step d) comprises at least a crystallisation operation from organic solvent. This embodiment is particularly advantageous when the starting mixture of the process mainly comprises triglycerides of azelaic acid and dicarboxylic acids having a carbon chain length >C9. Preferably, it is carried out by dissolving the organic phase evaporated and/or distilled in step c) in a hot organic solvent and crystallizing the dicarboxylic acids by cooling, advantageously under agitation. Suitable organic solvents are those listed above for use in step d1). Preferred are aliphatic hydrocarbons and more preferred are aliphatic alkanes such as, for example, hexane or octane, which advantageously allow obtaining satisfactorily pure dicarboxylic acids even at dissolution temperatures lower than 70° C. and with a solvent:organic phase ratio of below 1:5 by weight.

According to one aspect of the invention any dicarboxylic acids which are present in the aqueous phase separated in step b) undergo at least one of the recovery operations in step d), whether these are carried out through extraction in the presence of an organic solvent or through melt crystallisation, together or separately with respect to the fraction rich in dicarboxylic acids evaporated and/or distilled in step c). Before undergoing the recovery operations in step d) the said dicarboxylic acids present in the aqueous phase separated during step b) optionally undergo suitable treatments with the aim of removing them from the aqueous phase.

The process according to this invention is particularly suitable for the preparation of purified azelaic acid. Through this process it is in fact possible to obtain azelaic acid having a degree of purity over 90% and having a dicarboxylic acids content of 99.5% or more.

The process according to the invention may be carried out in either batch mode or continuous mode.

The process according to the invention will now be described with reference to non-limiting examples.

EXAMPLES

Preparation of the Mixture of Triglycerides Containing More than One Acid Functional Group The following were continuously fed to the first of 4 CSTR reactors placed in series, fitted with a stirrer and a suitable temperature regulating system:
 sunflower oil having a high oleic acid content (82% oleic, 10% linoleic, 4.5% palmitic, 3.5% stearic; throughput 100 kg/h);
 tungstic acid solution (throughput 19.2 kg/h).

The catalyst solution was prepared by continuously feeding 300 g/h of tungstic acid (0.35% in moles with respect to the moles of unsaturations) and 18.9 kg/h for 49% aqueous hydrogen peroxide solution) to a dissolver.

The remaining aqueous solution of 49% hydrogen peroxide was fed to the other reactors with an overall throughput of aqueous $H_2O_2$ to the 4 reactors of approximately 28 kg/h.

The reaction was carried out at 62° C. under vacuum (absolute pressure 0.1-0.2 bar) to evaporate the water delivered together with the hydrogen peroxide; the gas evaporated was collected and condensed (approximately 14 kg/h of water).

112 kg/h of an intermediate product containing vicinal diols was obtained and this was fed to the first of 4 identical reactors of the jet-loop type placed in series together with:
 cobalt acetate ($Co(CH_3COOH)_2 \cdot 4H_2O$) dissolved in a flow of water (of which it constituted 1.5% by weight; throughput 30 kg/h);
 compressed air (20 bar; throughput 125-128 kg/h).

The air flow was controlled in such a way as to maintain the $O_2$ content at the outlet from the reactor constant (approximately 10-12%). The reaction was performed at 72° C.

10% by weight of octane was added to the reaction product leaving the last reactor and an aqueous phase was separated by decanting, yielding approximately 137 kg/h of oily product.

The separated oily product was then deoctanised, dried and degassed, and then passed to a thin film evaporator. The vapour phase produced in the evaporator essentially contained pelargonic acid (approximately 31 kg/h) and lighter monocarboxylic acids.

An organic flow of approximately 86 kg/h, containing triglycerides with more than one carboxyl functional group as the major component, was drawn off from the base of the evaporator.

Example 1

Step a): Hydrolysis

The organic flow prepared as described above was pumped at high pressure to a hydrolysis reactor of the tubular type where it was mixed with a flow of preheated water. The overall throughput of the water/oil mixture was approximately 260 kg/h.

The reactor operated under conditions of 300° C. and 105 bar for a reaction time of 20 minutes.

Step b): Separation of Glycerine

The hydrolysed reaction mixture was cooled to a temperature of between 80 and 85° C., a quantity of octane equal to 4% by weight was added and the mixture was decanted to separate out the aqueous phase containing glycerine from the organic phase.

Step c): Evaporation/Distillation of Carboxylic Acids

The organic phase rich in azelaic acid was washed with water (30% by weight, at a temperature of between 80 and 85° C.) counter-currently to bring the residual glycerine to a concentration of below 0.05% by weight. After being washed with water the organic phase was then dehydrated and deoctanised and passed to a thin film evaporator (head temperature 204° C.; heater temperature 245° C., pressure 5 mbar). A liquid flow of 23 kg/h comprising a mixture comprising triglycerides and their oligomers was drawn off from the bottom of the evaporator.

The vapour phase was fed to a distillation column through which a flow of 5.6 kg/h comprising a mixture of light monocarboxylic acids with a pelargonic acid content of approximately 70% by weight was distilled. Approximately 54.4 kg/h of a mixture of dicarboxylic acids (mainly azelaic acid) having a heavy monocarboxylic acids content of 10%-12% (essentially palmitic acid and stearic acid) was obtained from a lateral distillation cut.

Step d1): Extraction with Water

The mixture of dicarboxylic acids so obtained was diluted with water in a ratio of 1:1 by weight and subsequently fed to a rotating stirrer extraction column thermostatted at 85° C. with a throughput of 109 kg/h, subdivided into two feed sections.

Further water was fed to the second feed section achieving an overall throughput of 272 kg/h and an aqueous phase/organic phase ratio of approximately 5:1.

The aqueous phase leaving the first column was then fed to a second extraction column thermostatted to a temperature of 80° C., with a throughput of 320 kg/h, counter-currently with respect to a flow of octane (32 kg/h; approximately 10% by weight with respect to the aqueous phase), introduced from the base of the column.

Step d2): Crystallisation

The aqueous flow leaving the second extractor, containing a dissolved organic phase characterised by a monocarboxylic acids content of less than 0.5% by weight, was first heated to a temperature of 95° C. and then subjected to reduced pressure (150 mbar) in a first crystalliser, where rapid cooling to the boiling point of the liquid (56° C.) occurred, with a first concentration of the suspension. Subsequently the suspension was passed to a second crystalliser identical to the first, operating at an absolute pressure of 34 mbar, corresponding to a boiling point of the liquid of 28° C. In this way the suspension reached a solids concentration of approximately 18% by weight.

The suspension so obtained was passed to a holding tank to allow crystals to grow. 48 kg/h of azelaic acid with a purity of 97% was obtained after crystallisation, separation of the crystals and drying.

The invention claimed is:

1. A process for the preparation of purified dicarboxylic acids from a mixture containing triglycerides of carboxylic acids having more than one acid functional group comprising the steps of:
 a) hydrolysing said mixture containing triglycerides in the presence of water, obtaining a reaction product comprising dicarboxylic acids and glycerine;
 b) separating out an aqueous phase comprising at least a part of the glycerine from the remaining reaction product from step a) organic phase;
 c) evaporating and/or distilling the organic phase obtained from step b), separating out a residue; and
 d) recovering at least a part of the dicarboxylic acids from the organic phase evaporated and/or distilled in step c)

by means of at least one crystallisation operation, said step comprising the operations of:
  d1) extracting the organic phase evaporated and/or distilled in step c) with water in the presence of an organic solvent, obtaining an aqueous phase containing said dicarboxylic acids
  d2) crystallising out said dicarboxylic acids from said aqueous phase obtained in step d1), wherein said step d1) comprises at least one counter-current extraction operation.

2. The process according to claim 1 comprising, before step a) the steps of:
  1) reacting the triglycerides of unsaturated carboxylic acid with an oxidising agent and a catalyst activating an oxidation reaction of the olefin double bond to obtain an intermediate compound containing vicinal diols,
  2) reacting said intermediate compound containing vicinal diols with an oxidising agent containing molecular oxygen and a catalyst activating the oxidation reaction of the vicinal diols to carboxylic groups, obtaining monocarboxylic acids and triglycerides of carboxylic acids having more than one acid functional group; and
  3) separating out a fraction of said monocarboxylic acids obtaining a mixture comprising said triglycerides of carboxylic acids having more than one acid functional group.

3. The process according to claim 1 in which the hydrolysis reaction in step a) is performed using water only at a temperature of between 240-320° C. at pressures of between 40 and 110 bar.

4. The process according to claim 3 in which said reaction is carried out at a temperature of between 260 and 310° C. at pressures of between 67 and 100 bar in one or more tubular reactors (Plug Flow Reactors).

5. The process according to claim 4 in which the ratio between the quantity of water and the starting mixture is between 1:1 and 5:1 by weight.

6. The process according to claim 1 in which said step b) comprises one or more operations selected from decanting, centrifuging, degassing, addition of water or addition of one or more organic solvents immiscible with water.

7. The process according to claim 1 in which the aqueous phase separated in step b) is further purified by means of one or more crystallization operations to recover the dicarboxylic acids contained therein.

8. The process according to claim 1 in which a fraction containing monocarboxylic acids is separated out during step c).

9. The process according to claim 1 in which any dicarboxylic acids recovered from the aqueous phase separated in step b) undergo at least one of the recovery operations in step d).

10. The process according to claim 1 in which step d1) comprises:
  (i) a preliminary extraction operation, performed by placing a fraction of dicarboxylic acids originating from step c) in contact with a quantity of water such as to obtain an aqueous phase/organic phase ratio of between 1:1 and 10:1 at a temperature of between 75 and 90° C., and separating out a first organic phase comprising monocarboxylic acids from a first aqueous phase comprising dicarboxylic acids; and
  (ii) a second extraction operation, performed by placing said first aqueous phase comprising dicarboxylic acids in contact with an organic solvent and separating out a second organic phase comprising monocarboxylic acids from a second aqueous phase comprising dicarboxylic acid.

11. The process according to claim 1 in which at least part of the crystallisation mother liquors separated out in step d2) of the process are recycled to hydrolysis step a).

12. A process for the preparation of purified dicarboxylic acids from a mixture containing triglycerides of carboxylic acids having more than one acid functional group comprising the steps of:
  a) hydrolysing said mixture containing triglycerides in the presence of water, obtaining a reaction product comprising dicarboxylic acids and glycerine;
  b) separating out an aqueous phase comprising at least a part of the glycerine from the remaining reaction product from step a) organic phase;
  c) evaporating and/or distilling the organic phase obtained from step b), separating out a residue; and
  d) recovering at least a part of the dicarboxylic acids from the organic phase evaporated and/or distilled in step c) by means of at least one crystallisation operation, said step comprising at least one melt crystallisation of said dicarboxylic acids.

13. The process according to claim 12 in which said recovery step d) comprises fractional suspension crystallisation.

14. A process for the preparation of purified dicarboxylic acids from a mixture containing triglycerides of carboxylic acids having more than one acid functional group comprising the steps of:
  a) hydrolysing said mixture containing triglycerides in the presence of water, obtaining a reaction product comprising dicarboxylic acids and glycerine;
  b) separating out an aqueous phase comprising at least a part of the glycerine from the remaining reaction product from step a) organic phase;
  c) evaporating and/or distilling the organic phase obtained from step b), separating out a residue; and
  d) recovering at least a part of the dicarboxylic acids from the organic phase evaporated and/or distilled in step c) by means of at least one crystallisation operation, wherein the triglycerides of carboxylic acids mainly comprise azelaic acid and higher dicarboxylic acids and said recovery step d) comprises at least one crystallisation of said dicarboxylic acids from an organic solvent selected from aliphatic hydrocarbons.

15. The process according to claim 2 in which the hydrolysis reaction in step a) is performed using water only at a temperature of between 240-320° C. at pressures of between 40 and 110 bar.

16. The process according to claim 2 in which said step b) comprises one or more operations selected from decanting, centrifuging, degassing, addition of water or addition of one or more organic solvents immiscible with water.

17. The process according to claim 3 in which said step b) comprises one or more operations selected from decanting, centrifuging, degassing, addition of water or addition of one or more organic solvents immiscible with water.

18. The process according to claim 4 in which said step b) comprises one or more operations selected from decanting, centrifuging, degassing, addition of water or addition of one or more organic solvents immiscible with water.

19. The process according to claim 5 in which said step b) comprises one or more operations selected from decanting, centrifuging, degassing, addition of water or addition of one or more organic solvents immiscible with water.

20. The process according to claim 2 in which the aqueous phase separated in step b) is further purified by means of one or more crystallization operations to recover the dicarboxylic acids contained therein.

* * * * *